United States Patent

Vercauteren et al.

[11] Patent Number: 5,773,606
[45] Date of Patent: Jun. 30, 1998

[54] CATALYST REGENERATION

[75] Inventors: Ronny Leontina Marcel Vercauteren, Sint-Niklaas; Myriam Elseviers, Kampenhout, both of Belgium

[73] Assignee: Cerestar Holding B.V., AA Sas Van Gent, Netherlands

[21] Appl. No.: 550,707

[22] Filed: Oct. 31, 1995

[30] Foreign Application Priority Data

Oct. 31, 1994 [GB] United Kingdom .................. 9421894

[51] Int. Cl.$^6$ ....................................... C07H 1/00
[52] U.S. Cl. ..................... 536/124; 536/1.11; 536/18.5; 536/125
[58] Field of Search ................... 536/1.11, 18.5, 536/125, 124

[56] References Cited

U.S. PATENT DOCUMENTS 4,029,878  6/1977  Kruse ..................... 536/18.5

FOREIGN PATENT DOCUMENTS

| 0 009 887 | 4/1980 | European Pat. Off. . |
| 2 029 719 | 3/1980 | United Kingdom . |
| 89/07602 | 8/1989 | WIPO . |

*Primary Examiner*—Elli Peselev
*Attorney, Agent, or Firm*—Pillsbury, Madison & Sutro LLP; Cushman Darby & Cushman Intellectual Property Group

[57] ABSTRACT

The present invention relates to the regeneration of a supported molybdenum catalyst which has been used for the epimerisation of a saccharide. The preferred epimerisation is the conversion of glucose to mannose. The catalyst is regenerated by using an oxidising agent such as a peroxide. The regeneration step can be repeated several times. A further extension of the useful lifetime of the catalyst is obtained by including one or more washing steps.

19 Claims, No Drawings

CATALYST REGENERATION

FIELD OF THE INVENTION

The present invention relates to the regeneration of a catalyst, in particular to the regeneration of a supported molybdenum catalyst especially a supported molybdenum catalyst which has been used for the epimerisation of a saccharide such as glucose.

BACKGROUND OF THE INVENTION

Saccharide epimerisation reactions are well known and it is in particular known that glucose may be epimerised to give an equilibrium mixture of glucose and mannose by means of a hexavalent molybdenum catalyst. The earliest reference to this reaction is by V. Bilik in Chem. Zvesti, 26, 183–186 (1972) while U.S. Pat. No. 4,029,878 (Jun. 14, 1977) contains a description of a process using the catalytic reaction. The patent further discloses the hydrogenation of the mannose produced in the process to mannitol, a compound useful as an ingredient of pharmaceutical tablets, and as a sweetener, humectant and chemical intermediate. Examples of suitable hexavalent molybdenum catalysts disclosed in U.S. Pat. No. 4,029,878 include molybdic acid, isopolymolybdic acids, heteropolymolybdic acids and acid salts such as sodium phosphomolybdate and silicomolybdic acid. This patent further describes the possibility of using as catalyst an anion exchange resin in which the hydroxyl ions have been replaced by molybdate ions. An example of this is given using molybdic acid supported on AMBERLYST A-26 a macroporous styrene-divinyl benzene quaternary anion exchange resin.

Japanese patent JP 55076894 discloses the use of molybdate immobilised on anion exchange fibers. When the activity of the molybdate-anion exchange fibre conjugate diminishes, the epimerisation process is stopped and the exhausted catalysator is leached off with alkali. Immobilisation of fresh molybdic acid on the original anion exchange fibre ensures a new active molybdate-anion exchange fiber conjugate.

European Patent 0 400 641 B1 also describes the use of molybdate exchanged anion exchange resin for epimerisation purposes. In this patent the process parameters are optimised in such a way that a minimal amount of bound molybdenum is leached of during epimerisation.

Japanese patent publication (JP 4-368347, published 21 Dec., 1992), commenting on U.S. Pat. No. 4,029,878 states that molybdic acid supported on an anion exchange resin such as AMBERLYST A-26 is not suitable for industrial application because the catalytic activity declines too rapidly during use. Nevertheless, the process disclosed in this patent application describes the use of a supported catalyst o n a macroporous, strongly basic anion exchange resin.

All catalysts mentioned above show an undesired reduction of activity during operation. To retain the desired conversion level of glucose to mannose a progressive reduction of the flow rate through the catalyst bed is required.

The advantage of using a supported molybdenum catalyst instead of an unsupported molybdenum compound lies in the fact that there is far less molybdenum in the aqueous epimerisation product which means that there are fewer separation and effluent disposal problems. The progressive diminution of the activity of the supported catalyst is, however, a disadvantage and even if the catalyst support is chosen so as to reduce the rate of the loss of activity, a time is reached when the activity is so low that it is no longer economic to continue to use the catalyst which must be replaced. A process using such a catalyst cannot be operated continuously because of interruptions for catalyst replacement.

SUMMARY AND OBJECTS OF THE INVENTION

We have now devised a process in which the activity of a supported molybdenum epimerisation catalyst may be renewed in situ without the need for catalyst removal. Although not fully continuous, our process is far closer to continuous operation than the processes previously described in which a supported molybdenum catalyst is employed.

The present invention relates to a process for the epimerisation of a saccharide which includes the regeneration of a supported molybdenum catalyst. The preferred epimerisation is the conversion of glucose to mannose. The catalyst is regenerated by using an oxidising agent such as peroxide. The regeneration step can be repeated several times. A further extension of the useful lifetime of the catalyst is obtained by including one or more washing steps.

DETAILED DESCRIPTION OF THE INVENTION

According to the invention therefore a process for the epimerisation of a saccharide by contacting an aqueous solution of the saccharide with a supported hexavalent molybdenum catalyst is characterised by a catalyst regeneration step in which the feed of aqueous saccharide to the catalyst is interrupted and the catalyst is treated with an oxidising agent so as to renew the depleted catalyst activity.

For reasons of convenience it is preferred to treat the catalyst with an aqueous solution of an oxidising agent so that use may be made of the system by which the aqueous saccharide solution is fed to the catalyst. Peroxides are suitable oxidising agents for use in the process, particularly hydrogen peroxide. Thus, an aqueous solution of hydrogen peroxide containing 0.1 to 30% hydrogen peroxide by weight may be used to regenerate the catalyst but it is preferred to use a 0.1 to 5% solution, because we have found that the higher the hydrogen peroxide content of the aqueous regenerating solution the greater the amount of molybdenum leached from the supported catalyst. The solution of oxidising agent may be recycled by means of a circulatory system to avoid wastage. Alternatively the solution is pumped through the molybdate-ion exchange conjugate in an open loop system.

The catalyst is preferably treated with the oxidising agent at an elevated temperature, suitably at a temperature in the range 30° C. to the temperature at which the catalyst support is no longer stable preferably at a temperature in the range 40° to 120° C. and more preferably in the range 70° to 95° C.

The pH of the aqueous solution of the oxidising agent is preferably in the range 0.5 to 7, more preferably in the range 1.0 to 5.5 since higher pH conditions lead to an increased leaching of molybdenum from the catalyst support.

During operation of Molybdate-carrier conjugates at high temperature, organic substances are adsorbed irreversibly on the resin, this results in clogging of the pores and micropores of the resin. The active Molybdate sites are covered and the catalytic activity is diminished considerably. This phenomenon is known as organic contamination (fouling). The organic substances in the used syrup (carbohydrates, proteins and other organic contaminants) may even polymerise over long periods of time.

In or der to remove this organic deposit on the resin, contacting with a solvent or solution which desorbs the organic substances from the resin surface is necessary. This solvent can be water, a solution of a salt and/or an oxidising agent in water. Also an organic eluotropic (Y. Pomeranz, C. E. Meloan, Food Analysis : Theory and Practice, Third Ed., Chapman & Hall, New-York, 343–344, 1994, and C. Seaver, J. Przybytek, LC-GC Int., 8(4), 190–195, 1995) solvent like propanol, ethanol, methanol, acetonitile or glycol can be used. Mixtures of different solvents with or without water can also be used. In fact, any solvent system which can desorb organic matter from the carrier surface can be used. The desorption can be done at ambient or elevated temperature and at preferably a pH where no substantial leaching of Mo is observed.

The cleaning procedure can be carried out at any time during operation. The lifetime of the Mo-carrier conjugate is thereby considerably extended. Preferably the cleaning procedure is performed before a reactivation with an oxidising agent.

Examples 1, 2 and 3 disclose that after regeneration of the catalyst the conversion level is increased considerably.

In Example 2 it is shown that where the starting values were 25–26% mannose in the product stream at a flow rate of 2 bed volumes/per hour the regenerated catalyst had recovered 100% of the initial activity whereas the desired conversion before regeneration (29 days) could only be reached with a flow rate of 0.5 bed volumes per hour.

Examples 4, 5 and 6 illustrate that cleaning of the catalyst in the column with different solvents also considerably increases catalytic activity.

It is preferable to clean the catalyst before regeneration.

The epimerisation reaction to which the process of the present invention is particularly applicable is the epimerisation of glucose to mannose. For this process the molybdenum catalyst is generally considered to need regeneration when the flow-rate to obtain 25% mannose (by weight) is decreased to 0.5 Bed Volume/hr. At this stage the catalyst manifests an intense dark blue colouration which progressively disappears during the regeneration process. The complete disappearance of the blue colour is taken as indicative that the regeneration is complete and that the feed of glucose to the catalyst may be restarted. Epimerisation processes to which the present invention is applicable are manifold.

The reactants or feedstocks in the epimerization reaction are solutions, generally aqueous solutions, containing at least one aldose or aldose analog. An aldose is a carbohydrate containing an aldehyde group. Those with 4 carbons are called tetroses, those with 5 carbons are called pentoses, those with 6 are called hexoses, those with 7 heptoses, and so forth. The tetroses consist of erythrose and threose. Included in the pentoses are ribose, arabinose, xylose, and lyxose. The hexoses contain allose, altrose, glucose, mannose, gulose, idose, galactose, and talose. Although the aldohexoses as a group may be the most important, the epimeric aldopentoses; ribose and arabinose, are also important in the practice of this invention.

It is believed that the essential structural unit for epimerization by molybdate is,

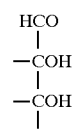

and any compound, other than an aldose itself, with such a unit may be called an aldose analog. Another class of aldose analogs consists of n-deoxy-aldoses where $n \geq 4$, i.e., aldoses whose hydroxyl group at carbon number n, C-n (where the aldehydic carbon is C-1) has been replaced by a hydrogen. This class is exemplified by rhamnose, 6-deoxy-glucose, 4-deoxy-lyxose, 5-deoxy-arabinose, 4-deoxy-mannose, and 5-deoxy-talose. Another class includes aldose esters and ketals where ester and/or ketal formation occurs at C-n, with $n \geq 4$. Examples include glucose-6-acetate, mannose-5,6-dibutyrate, 4,6-O-ethylidene-mannose, and so forth. Another class is that of the uronic acids, i.e., hexoses whose hydroxymethyl at C-6 has been converted to the carboxylic acid group, and the alduronic acids, as exemplified by glucuronic acid, mannuronic acid, galacturonic acid, and so forth. Still another class is that of the 6-deoxy-6-amino-aldoses, i.e., aldoses whose hydroxyl at C-6 has been replaced by an amino group. 4, 5, or 6-O-alkyl aldoses are glycosides which also are suitable aldose analogs, as are the 4-, 5- or 6-deoxy haloaldoses. Another class of aldose analogs are the oligosaccharides such as maltose, isomaltose, melibiose, isomaltotriose, palatinose, gentiobioses, laminaribiose.

The support for hexavalent molybdenum catalyst may be chosen from those supports previously suggested for the purpose in the prior art, particularly in the prior art referred to above. Preferably the support is an anion exchange resin, more preferably a strongly basic anion exchange resin especially a macroporous, strongly basic anion exchange resin. Such strongly basic resins generally have a quaternary ammonium functional group and are preferably stable at temperature at least as high as 100° C.

The molybdenum compound mounted on or in the support may be any hexavalent molybdenum compound useful for this purpose. Suitable compounds have already been reported in the prior art. Preferably, the molybdenum compound is molybdic acid or a salt thereof e.g. ammonium or sodium molybdate. The supported catalyst is prepared by contacting the support with an aqueous solution of the molybdenum compound suitably at ambient temperature for a period of time sufficient to achieve the desired loading of the catalyst on the support eg. up to 72 hours. The pH of the solution of the molybdenum compound in contact with the support is advantageously in the range 0.5 to 7, preferably 1.0 to 5.5. The preferred loading of the molybdenum compound catalyst on the support will vary from support to support but may be determined by simple experiment. Too high a loading for a given support should be avoided because of the disadvantage of an increased leaching of molybdenum from the support into the solution during the epimerisation reaction.

The saccharide, eg. solution fed to the catalyst suitably comprises 10 to 60% by weight dry substance, preferably 20 to 50% by weight. The epimerisation reaction may be carried out at a temperature in the range 70° to 160° C. preferably 70° to 100° C. and at a pH of the feed solution in the range 0.5 to 7, preferably 1.0 to 5.5.

The catalyst regeneration step and the washing step can be repeated several times before the final activity of the catalyst becomes to low to be useful. It is therefore apparent from the examples that the present invention considerably extends the useful lifetime of the catalyst and thereby reduces the process costs.

The invention will now be further illustrated by reference to the following Examples.

EXAMPLES

Example 1

The resin used was DOWEX MSA1 a macroporous, strongly basic, anion-exchange resin (DOWEX is a trademark). The resin was immersed in an aqueous solution containing 250 grams/litre of sodium molybdate for a period of 12 hours. A trace of hydrogen peroxide (0.3 grams/litre) was added to the sodium molybdate solution which had a pH of 3.5. The loading of the sodium molybdate on the support was 128.4 grams/litre resin expressed as elemental molybdenum.

100 mls of the supported catalyst prepared as described in the preceding paragraph were placed in a glass column 40 cm long and 2.5 cm diameter. A 50% ds glucose solution was fed to this column at a rate of 0.5 bed volumes/hour the temperature of the column was held at 90° C. and the pH of the feed solution at 3.5.

The epimerisation reaction product initially contained 30% by weight (based on dry substance) of mannose but over a period of 17 days the amount fell to below 25%. At this value the glucose feed was interrupted and the catalyst bed, which exhibited a blue colour, was back-washed with 2.0 bed volumes of a 1% hydrogen peroxide solution at 90° C. for one hour. The pH of the hydrogen peroxide solution was 3.5 and during this treatment the blue colour of the bed disappeared. The feed of glucose solution was then recommenced and the amount of mannose in the epimerisation product was once again found to be about 30%.

Example 2

This example describes the production of a 25% (w/w) mannose containing syrup out of a syrup containing 97.1% glucose, 2.1% $DP_2$ (disaccharides), 0.3% $DP_3$ (trisaccharides) and 0.5% $\geq DP_4$ (tetrasaccharides and higher).

15,8 g of $Na_2 Mo O_4.2H_2O$ were dissolved in 80 ml of demi water and the pH was brought to 3.5 with $H_2SO_4$ (96% w/w, 5 times diluted). This solution was added to 50 ml of DOWEX MSA-1 which had been washed with 400 ml of $H_2O$. The resin was stirred until all molybdate was bound. During the immobilisation, the pH was continuously adjusted to pH 3.5.

The molybdate-DOWEX MSA-1 conjugate was brought on a column (double jacketed glass column), and heated to 90° C. A 40% ds glucose solution at pH 2 was fed to this column. The flow rate was adjusted to obtain continuously a solution containing 25–26% mannose (flow-rate at start: 2 bed volumes per hour (bv/h)). After 29 days, the flow-rate had dropped to 0.5 bv/h. The conjugate was washed with $H_2O$ until no sugars were detectable in the effluent (refractive index determination). Subsequently, 5bv of a 1.5% $H_2O_2$ aqueous solution were fed to the column at 90° C. at 2.5 bv/h. Afterwards the conjugate was washed with 5bv of $H_2O$ and the epimerisation was continued, giving a product containing 25.6% mannose at 2.1 bv/h.

Example 3

36 g of $Na_2 Mo O_4$ was dissolved in 160 ml of demi water and the pH was adjusted to 3.5 with $H_2O$. This solution was circulated through a glass column, filled with 100 ml Lewatit® MP-500 (Bayer). After complete immobilisation of the molybdate, the resin was washed with 10 bv of $H_2O$.

The substrate from example 2 was send through the conjugate at 40% ds glucose and 90° C. pH 2. Initital flow-rate was 2bv/h and gave 25% mannose. After 29 days, the flow-rate had dropped to 0.6 bv/h giving a product containing 25.3% mannose. The conjugate was rinsed on-column with $H_2O$ i.e until no sugars could be detected in the effluent any more and reactivated with 5 bv of a 3% $H_2O_2$ solution at 5 bv/h. Subsequently, the conjugate was rinsed with 10 bv $H_2O$ and epimerisation was continued giving a product containing 25.6% mannose at 1.5 bv/h.

Example 4

The same immobilisation procedure as exemplified in example 2 was used to prepare the Molybdate-Dowex MSA-1 conjugate. The operational conditions were equivalent to those described in example 2. At day 0, the substrate feeding to the conjugate was stopped and the conjugate was washed with water until no sugars could be detected in the effluent any more. The temperature was decreased to ambient temperature and the conjugate stood for 6 days on water. Subsequently the conjugate was rinsed with 5 bed volumes of water and the temperature of the column was increased to 90° C. and syrup (at pH 2) was sent through the conjugate at 40% ds. The results are given in following table:

| Days | Flow rate (BV/h) | % Mannose (w/w) |
| --- | --- | --- |
| −2 | 1.0 | 25.3 |
| −1 | 1.0 | 25.3 |
| 0 | 0.9 | 25.4 |
| 1 | 1.1 | 26.2 |
| 2 | 0.8 | 26.2 |
| 3 | 0.9 | 26.3 |

Day 0 is the actual day of rinsing of the conjugate. Day 1 is the first day after the cleaning on which the conjugate is put back in operation.

Example 5

The same immobilisation procedure as exemplified in example 2 was used to prepare the Molybdate-Dowex MSA-1 conjugate. The operational conditions were equivalent to those described in example 2.

At day 0, the substrate feeding to the conjugate was stopped and the conjugate was washed with water until no sugars could be detected in the effluent any more.The temperature was decreased to ambient temperature and the conjugate was washed during night with water at 1.0 BV/h. Thereafter, the temperature of the column was increased to 90° C. and syrup (at pH 2) was sent through the conjugate at 40% ds. The results are given in following table:

| Day | Flow-rate (BV/h) | % Mannose (w/w) |
| --- | --- | --- |
| −1 | 1.2 | 24.8 |
| 0 | 1.0 | 25.4 |
| 1 | 1.0 | 26.3 |
| 2 | 1.3 | 25.8 |

Day 0 is the actual day of rinsing of conjugate. Day 1 is the first day after the cleaning on which the conjugate is put back in operation.

Example 6

The same immobilisation procedure as exemplified in example 2 was used to prepare the Molybdate-Dowex MSA-1 conjugate. The operational conditions were equivalent to those described in example 2.

At day 0, the substrate feeding to the conjugate was stopped and the conjugate was washed with water until no sugars could be detected in the effluent any more. The temperature was decreased to ambient temperature and the conjugate was washed during night with one of the following solvents : 50% iso-propanol/50% demi water (v/v), 50% ethanol/50% demi water (v/v) or 50% acetonitrile/50% demi water at 1.0 BV/h. Thereafter the conjugate was rinsed with 5 BV water, the temperature of the column was increased to 90° C. and syrup (at pH 2) was sent through the conjugate at 40% ds.

The results are given in following tables a) Solvent: 50% ethanol/50% demi water (v/v)

| Day | Flow rate (BV/h) | % Mannose (w/w) |
| --- | --- | --- |
| −1 | 1.2 | 24.7 |
| 0 | 0.7 | 26.1 |
| 1 | 1.3 | 25.8 |

Day 0 is the actual day of rinsing of conjugate. Day 1 is the first day after the cleaning on which the conjugate is put back in operation.

b) 50% iso-propanol/50% demi water (v/v)

| Day | Flow-rate (BV/h) | % Mannose (w/w) |
| --- | --- | --- |
| −1 | 1.3 | 25.0 |
| 0 | 0.9 | 26.2 |
| 1 | 1.3 | 26.6 |

Day 0 is the actual day of rinsing of conjugate. Day 1 is the first day after the cleaning on which the conjugate is put back in operation.

c) 50% acetonitrile/50% demi water (v/v)

| Day | Flow-rate (BV/h) | % Mannose (w/w) |
| --- | --- | --- |
| −1 | 1.2 | 24.0 |
| 0 | 0.8 | 26.2 |
| 1 | 1.0 | 27.3 |

Day 0 is the actual day of sweetening off of conjugate. Day 1 is the first day after the cleaning on which the conjugate is put back in operation.

We claim:

1. A process for the epimerisation of a saccharide which comprises the steps of
    (a) contacting an aqueous feed comprising an aqueous solution of the saccharide with a supported hexavalent molybdenum catalyst; and
    (b) regenerating the activity of the supported hexavalent molybdenum catalyst by interrupting the said aqueous feed and treating said supported hexavalent molybdenum catalyst with an aqueous solution of peroxide having a pH of 0.5 to 7 as an oxidising agent.
2. A process according to claim 1, wherein the aqueous solution of a peroxide is a 0.1 to 30% by weight solution of hydrogen peroxide.
3. A process according to claim 1, wherein the catalyst is treated with the oxidizing agent at a temperature in the range 30° C. to the temperature at which the catalyst support is no longer stable.
4. A process according to claim 1, wherein the epimerisaton is the conversion of glucose to mannose.
5. A process according to claim 1, wherein the catalyst support is an anion exchange resin.
6. A process according to claim 1, wherein the hexavalent molybdenum compound mounted on or in the support is molybdic acid or a salt of molybdic acid.
7. A process according to claim 1, wherein the saccharide solution fed to the catalyst comprises 10 to 70% by weight dry substance.
8. A process according to claim 1, wherein said process further comprises, in addition to the catalyst regeneration step, a catalyst washing step.
9. A process according to claim 8 wherein the catalyst washing step is performed with water, a solution of a salt and/or an oxidising agent in water, an eluotropic organic solvent or mixtures thereof.
10. A process according to claim 1, wherein said oxidizing agent comprises hydrogen peroxide.
11. A process according to claim 1, wherein said oxidizing agent comprises a 0.1 to 5% by weight solution of hydrogen peroxide.
12. A process according to claim 1, wherein in the catalyst regeneration step the treatment with said oxidizing agent is effected at a temperature in the range of 40° C.–120° C.
13. A process according to claim 1, wherein in the catalyst regeneration step the treatment with said oxidizing agent is effected at a temperature in the range of 70° C.–95° C.
14. A process according to claim 1, wherein oxidizing agent is in a solution which has a pH in the range of 1.0 to 5.5.
15. A process according to claim 5, wherein said anion exchange resin comprises a macroporous, strongly basic anion exchange resin.
16. A process according to claim 6, wherein said hexavalent molybdenum compound is sodium molybdate or ammonium molybdate.
17. A process according to claim 2, wherein the catalyst is treated with the oxidizing agent at a temperature in the range of 30° C. up to the temperature at which the catalyst support is no longer stable.
18. A process for epimerizing glucose to mannose which comprises the steps of:
    (a) contacting an aqueous feed comprising an aqueous solution of the glucose and a supported hexavalent molybdenum catalyst under conditions effective for epimerizing glucose and allowing the epimerization reaction to proceed until the flow rate to attain a 25% by weight conversion to mannose decreases to a determined value; and
    (b) interrupting said aqueous feed and heating said supported hexavalent molybdenum catalyst with an amount of hydrogen peroxide effective to renew catalyst activity; and
    optionally resuming said contacting step (a).
19. A process for the epimerisation of a saccharide which comprises the steps of:
    (a) contacting an aqueous feed consisting essentially of an aqueous solution of the saccharide and a hexavalent molybdenum catalyst supported on an anion exchange resin; and
    (b) regenerating the activity of the hexavalent molybdenum catalyst supported on the anion exchange resin by interrupting said aqueous feed and treating said hexavalent molybdenum catalyst supported on an anion exchange resin with an aqueous solution of a peroxide which has a pH of 0.5 to 7; and
    (c) optionally repeating step (a) and step (b).

* * * * *